US012670973B2

(12) United States Patent
Galassi

(10) Patent No.: US 12,670,973 B2
(45) Date of Patent: *Jun. 30, 2026

(54) PROVIDING SECURE AND SEAMLESS AUTHENTICATION AND WORKFLOW FOR MEDICAL RECORDS AND AFFILIATED SYSTEMS

(71) Applicant: Christopher R. Galassi, Schaumburg, IL (US)

(72) Inventor: Christopher R. Galassi, Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,239

(22) Filed: Apr. 3, 2020

(65) Prior Publication Data

US 2021/0158910 A1     May 27, 2021

Related U.S. Application Data

(63) Continuation of application No. 14/567,829, filed on Dec. 11, 2014, now Pat. No. 10,614,911.

(60) Provisional application No. 61/914,898, filed on Dec. 11, 2013.

(51) Int. Cl.
| | |
|---|---|
| *G06F 19/00* | (2018.01) |
| *G16H 10/60* | (2018.01) |
| *G16Z 99/00* | (2019.01) |

(52) U.S. Cl.
CPC ............. *G16H 10/60* (2018.01); *G16Z 99/00* (2019.02)

(58) Field of Classification Search
CPC ............................... G16H 10/60; G16Z 99/00
See application file for complete search history.

(56) References Cited

U.S. PATENT DOCUMENTS

| | | | |
|---|---|---|---|
| 2004/0069311 A1 | 4/2004 | Sasaki et al. | |
| 2007/0027715 A1 | 2/2007 | Gropper et al. | |
| 2012/0215560 A1* | 8/2012 | Ofek ...................... | G16H 10/00 705/3 |
| 2014/0136237 A1 | 5/2014 | Anderson et al. | |
| 2014/0249850 A1 | 9/2014 | Woodson et al. | |
| 2015/0073829 A1* | 3/2015 | Newman ................ | G16H 10/20 705/3 |

* cited by examiner

*Primary Examiner* — Maroun P Kanaan
(74) *Attorney, Agent, or Firm* — McDonnell Boehnen Hulbert & Berghoff LLP

(57) ABSTRACT

Methods and systems are provided that are related to electronic health records (EHRs). A first EHR system can receive a request to report information to a second EHR system. Responsive to the request, the first EHR system can generate an EHR report that includes one or more EHR identifiers. The one or more EHR identifiers can include an EHR-user identifier, an EHR-patient identifier, and a behavior identifier. The first EHR system can send the EHR report to the second EHR system. The second EHR system can: access information based on the EHR-user identifier and/or the EHR-patient identifier, generate an output based on the accessed information, and provide the output.

20 Claims, 10 Drawing Sheets

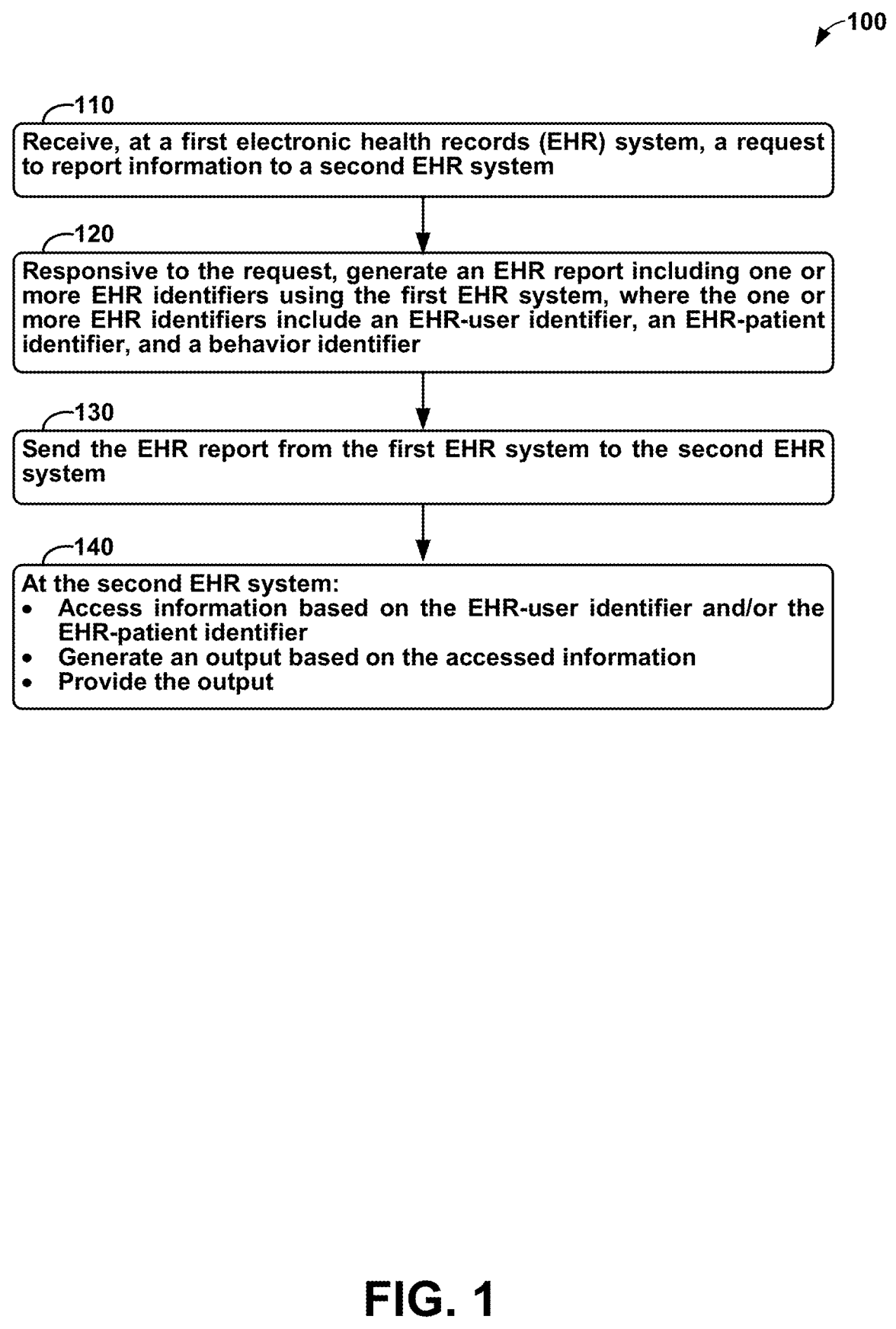

┌─ 100

┌─ 110
┌──────────────────────────────────────────────────────────┐
│ Receive, at a first electronic health records (EHR) system, a request │
│ to report information to a second EHR system                │
└──────────────────────────────────────────────────────────┘

┌─ 120
┌──────────────────────────────────────────────────────────┐
│ Responsive to the request, generate an EHR report including one or │
│ more EHR identifiers using the first EHR system, where the one or │
│ more EHR identifiers include an EHR-user identifier, an EHR-patient │
│ identifier, and a behavior identifier                      │
└──────────────────────────────────────────────────────────┘

┌─ 130
┌──────────────────────────────────────────────────────────┐
│ Send the EHR report from the first EHR system to the second EHR │
│ system                                                     │
└──────────────────────────────────────────────────────────┘

┌─ 140
┌──────────────────────────────────────────────────────────┐
│ At the second EHR system:                                  │
│ • Access information based on the EHR-user identifier and/or the │
│   EHR-patient identifier                                   │
│ • Generate an output based on the accessed information      │
│ • Provide the output                                       │
└──────────────────────────────────────────────────────────┘

FIG. 1

700
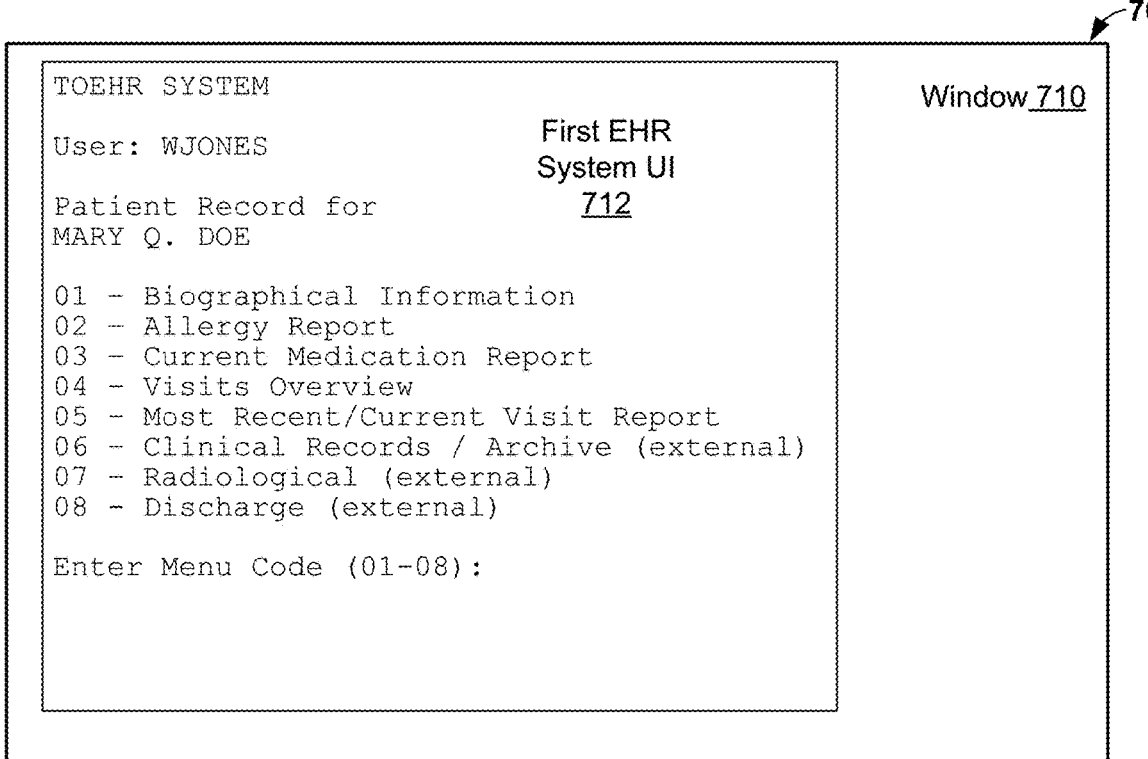
TOEHR SYSTEM
User: WJONES
First EHR
System UI
712
Patient Record for
MARY Q. DOE
01 – Biographical Information
02 – Allergy Report
03 – Current Medication Report
04 – Visits Overview
05 – Most Recent/Current Visit Report
06 – Clinical Records / Archive (external)
07 – Radiological (external)
08 – Discharge (external)
Enter Menu Code (01-08):
Window 710
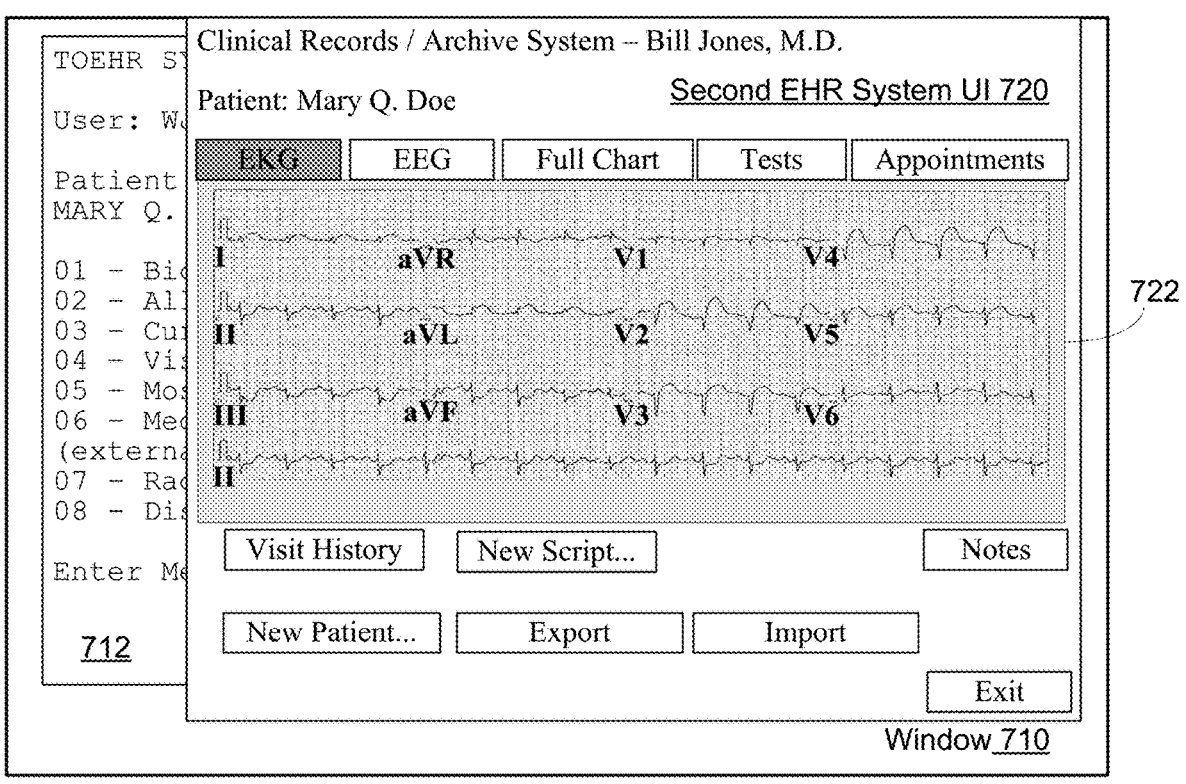
FIG. 7

Radiological EHR System 800

User Identifier 810

Patient Identifier 812

Image Identifier 816

Image Display 820

Notes Region 830

832

UI Controls 840

PROVIDING SECURE AND SEAMLESS AUTHENTICATION AND WORKFLOW FOR MEDICAL RECORDS AND AFFILIATED SYSTEMS

CROSS REFERENCE TO RELATED APPLICATIONS

This application is a continuation of U.S. patent application Ser. No. 14/567,829, filed Dec. 11, 2014, entitled "Providing Secure and Seamless Authentication and Workflow for Medical Records and Affiliated Systems," which claims priority to U.S. Patent App. No. 61/914,898, entitled "Providing Secure and Seamless Authentication and Workflow for Medical Records and Affiliated Systems," filed Dec. 11, 2013, the contents of which are fully incorporated by reference herein for all purposes.

BACKGROUND

Electronic health record (EHR) systems are used to systematically collect health information about individual patients or populations and store the collected information in an electronic format. The collected information can be shared between EHR systems that utilize interfaces that operate according to agreed-upon standards, such as the Health Level 7 (HL7) series of standards.

However, use of multiple EHR systems can be inconvenient. For example, each EHR system often requires a separate authentication process, such as logging into the EHR system. Further, once logged in to a EHR system, the EHR system often starts at a predefined starting location, such as a providing an introductory prompt or home screen. If a user has to switch between EHR systems while performing a task, restarting at a starting location can cause delay. Further, upon switching systems, the user often has to re-enter data already provided to an EHR system, which causes delays at best, and can introduce errors due to incorrectly entered information. Also, while information can be interchanged using HL7 or other interfaces, delivery of HL7 data is not guaranteed to occur in real-time or near real-time; e.g., within one minute or less.

SUMMARY

In one aspect, a method is provided. A first electronic health records (EHR) system receives a request to report information to a second EHR system. Responsive to the request, the first EHR system generates an EHR report that includes one or more EHR identifiers. The one or more EHR identifiers include an EHR-user identifier, an EHR-patient identifier, and a behavior identifier. The first EHR system sends the EHR report to the second EHR system. The second EHR system: accesses information based on the EHR-user identifier and/or the EHR-patient identifier; generates an output based on the accessed information; and provides the output.

In another aspect, a system is provided. The system includes a first EHR system and a second EHR system. The first EHR system receives a request to report information to a second EHR system. Responsive to the request, the first EHR system generates an EHR report that includes one or more EHR identifiers. The one or more EHR identifiers include an EHR-user identifier, an EHR-patient identifier, and a behavior identifier. The first EHR system sends the EHR report to the second EHR system. The second EHR system: accesses information based on the EHR-user identifier and/or the EHR-patient identifier, generates an output based on the accessed information; and provides the output.

In another aspect, a system is provided. The system includes a first EHR system and a second EHR system. The first EHR system includes: means for receiving a request to report information to the second EHR system; means for, responsive to the request, generating an EHR report including one or more EHR identifiers, where the one or more EHR identifiers include an EHR-user identifier, an EHR-patient identifier, and a behavior identifier; and means for sending the EHR report to the second EHR system. The second EHR system includes: means for accessing information based on the EHR-user identifier and/or the EHR-patient identifier; means for generating an output based on the accessed information; and means for providing the output.

In another aspect, a method is provided. An EHR system receives an EHR report. The EHR report includes one or more EHR identifiers. The one or more EHR identifiers include an EHR-user identifier, an EHR-patient identifier, and a behavior identifier. The EHR system accesses information based on the EHR-user identifier and/or the EHR-patient identifier. The EHR system generates an output based on the accessed information. The EHR system provides the output.

In another aspect, an EHR system is provided. The EHR system includes one or more processors and non-transient computer readable memory. The non-transient computer readable memory is configured to store executable instructions that, upon execution by the one or more processors, cause the EHR system to perform functions. The functions include: receiving an EHR report including one or more EHR identifiers, where the one or more EHR identifiers include an EHR-user identifier, an EHR-patient identifier, and a behavior identifier; accessing information based on the EHR-user identifier and/or the EHR-patient identifier; generating an output based on the accessed information; and providing the output.

In another aspect, a non-transient computer readable memory, configured to store executable instructions that, upon execution by one or more processors of a computing device, cause the computing device to perform functions. The functions include: receiving an EHR report including one or more EHR identifiers, where the one or more EHR identifiers include an EHR-user identifier, an EHR-patient identifier, and a behavior identifier; accessing information based on the EHR-user identifier and/or the EHR-patient identifier; generating an output based on the accessed information; and providing the output.

In another aspect, a device is provided. The device includes: means for receiving an EHR report including one or more EHR identifiers, where the one or more EHR identifiers include an EHR-user identifier, an EHR-patient identifier, and a behavior identifier; means for accessing information based on the EHR-user identifier and/or the EHR-patient identifier; means for generating an output based on the accessed information; and means for providing the output.

BRIEF DESCRIPTION OF THE DRAWINGS

FIG. 1 is a flowchart of a method, in accordance with an example embodiment.

FIG. 7 depicts a scenario for using user interfaces for two EHR systems, in accordance with an example embodiment.

DETAILED DESCRIPTION

Overview

Figure 2:
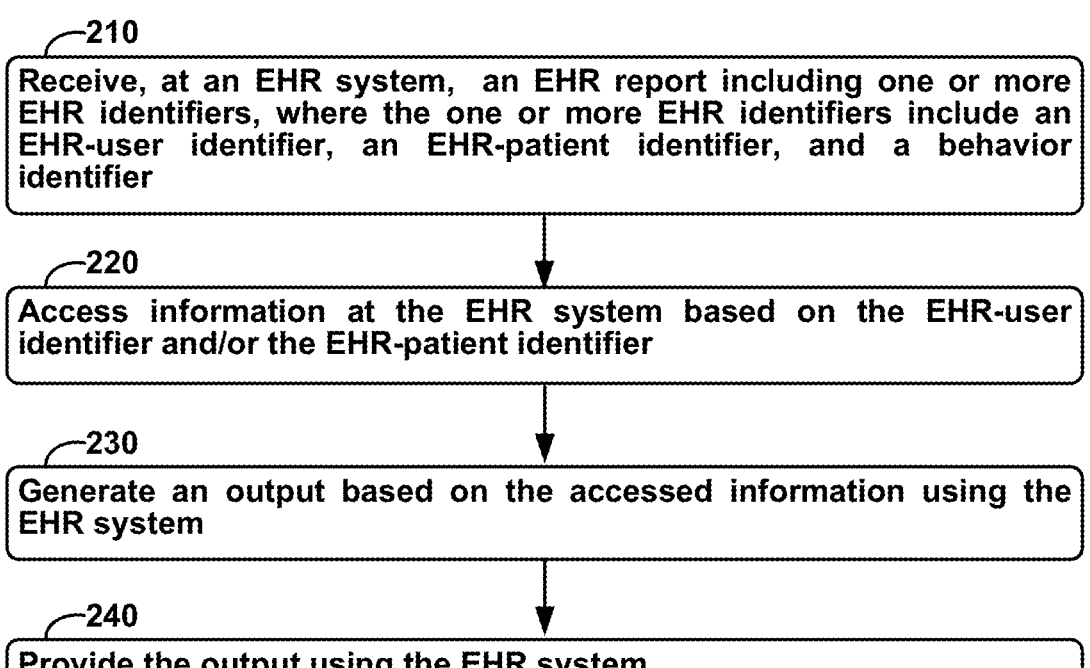
FIG. 2 is a flowchart of another method, in accordance with an example embodiment.

Apparatus and methods for simplifying use of EHR systems are provided. In particular, once a user of a first EHR system has been authenticated and selected a patient's records, data, such as authentication and patient selection data, can be reported to a second EHR system. The second EHR system can use the reported data to authenticate the user on the second EHR system and locate records on the second EHR system for the selected patient, without requiring data entry by the user for authentication or patient selection on the second EHR system.

In some cases, the second EHR system can be configured to provide data and/or functionality related to the selected patient that is difficult or impossible to achieve using the first EHR system alone. For example, the first EHR system may be a text-based system with a command line interface, and the second EHR system can provide a graphical interface to the text-based system. Another example of the second EHR system can be a patient discharge EHR system that can provide instructions to the patient upon discharge from a hospital or similar health facility. The patient discharge EHR system can also enable the user to order and/or provide other discharge-related items (e.g., prescriptions for post-discharge pharmaceuticals, appointments for post-discharge treatment, web addresses for more information). A third example of the second EHR system can be a radiological EHR system that enables display and other functionality of radiological records unavailable in using the text-oriented first EHR system. Many other examples are possible as well.

Data can be coordinated between the first and second EHR systems. For example, matching user identifiers, such as user pseudonyms, can be established on both EHR systems. Then, the report from the first EHR system can include the user pseudonym for a user authenticated to use the first EHR system and to request use of the second EHR system. Upon reception of the report, the second EHR system can obtain the user pseudonym from the report and attempt to locate a matching user pseudonym for the second EHR system. If the matching user pseudonym is found, the second EHR system can assume the user was authenticated by the first EHR system, and so authenticate the user to use the second EHR system.

The report can include other identifiers beyond the user identifier/pseudonym discussed above. For example, the report can include one or more patient identifiers, such as patient account numbers, patient identifiers, patient types, patient names, and/or patient pseudonyms, known to both the first and second EHR systems to identify patients. The patient identifier(s) provided in the report can be selected to identify a patient whose records are being processed on the first EHR system at the time of the report. Then, by identifying the current patient to the second EHR system, the second EHR system can be instructed to automatically find the records for the patient identified in the report. Thus, reporting of patient identifiers can enable ready extension of workflow for the current patient from the first EHR system and the second EHR system.

Other identifiers can include a behavior identifier to indicate a desired behavior for the second EHR system. For example, suppose the second EHR system can provide both patient discharge instructions and patient pre-admission instructions. Then, the first EHR system can use two different behavior identifiers in reporting to the second EHR system: one behavior identifier to request patient discharge instruction functionality and data, and another behavior identifier to request for patient pre-admission instruction functionality and data. A "machine" identifier can identify a computing device acting as the first EHR system; e.g., by name, fully qualified domain name (FQDN), Internet Protocol (IP) address, Media Access Control (MAC) address, Universal Resource Locator (URL), etc. An application identifier can identify software of the first EHR system being used at the time that use of the second EHR system is requested. A site identifier can indicate a location, medical facility name, address, site name, or other data to identify where the first EHR system is resident. Many other identifiers are possible as well.

Thus, functionality of the first EHR system can be extended by reporting user identifiers and other information to one or more second EHR systems. The second EHR systems can provide data and/or functionality not available using the first EHR system. Further, the second EHR systems can use patient identifiers in the report to extend workflow seamlessly between the first and second EHR systems, thus saving time, money, and possible patient discomfort by speeding and reducing errors during medical record processing.

Example Operations

FIG. 1 is a flowchart of method 100, in accordance with an example embodiment. Method 100 can be executed by one or more computing devices acting as one or more EHR systems. An example computing device is described as computing device 1100 discussed below at least in the context of FIG. 11.

Method 100 can begin at block 110, where a first EHR system can receive a request to report information to a second EHR system.

At block 120, in response to the request, the first EHR system can generate an EHR report. The EHR report can include one or more EHR identifiers. The one or more EHR identifiers can include an EHR-user identifier, an EHR-patient identifier, and a behavior identifier.

At block 130, the first EHR system can send the EHR report to a second EHR system.

In some embodiments, both the first EHR system and the second EHR system can store a record for a patient identified by the EHR-patient identifier.

In other embodiments, sending the EHR report can include receiving the EHR report at the second EHR system. The second EHR system can determine whether the EHR-user identifier identifies a new user of the second EHR system. In response to determining that the EHR-user identifier identifies a new user of the second EHR system, the second EHR system can add a user to the second EHR system, where the added user is identified by the EHR-user identifier.

In even other embodiments, sending the EHR report can include receiving the EHR report at the second EHR system. The second EHR system can determine whether the EHR-patient identifier identifies a new patient to the second EHR system. In response to determining that the EHR-user identifier identifies a new patient to the second EHR system, the second EHR system can add a patient to the second EHR system, where the added patient is identified by the EHR-patient identifier.

At block 140, the second EHR system can: access information based on the EHR-user identifier and/or the EHR-patient identifier, generate an output based on the accessed information, and provide the output.

In some embodiments, the second EHR system can include a patient discharge EHR system. In particular of these embodiments, the EHR-patient identifier can identify a patient being discharged from a medical facility. In more particular of these embodiments, the output can include one or more discharge instructions for the patient being discharged.

In other embodiments, the second EHR system can include a radiological EHR system. Then, the output can include a display of radiological information for a patient identified by the EHR-patient identifier.

In still other embodiments, providing the output using the second EHR system can include providing the output based on the behavior identifier using the second EHR system.

In yet other embodiments, the first EHR system can be configured to authenticate users before using the first EHR system, and the second EHR system can be configured to authenticate users before using the second EHR system. In some of these embodiments, method 100 can further include: prior to receiving the receiving the request to report the information to the second EHR system, authenticating a user associated with the EHR-user identifier to use the first EHR system; and prior to sending the EHR report from the first EHR system to the second EHR system, not authenticating the user associated with the EHR-user identifier to use the second EHR system. In particular of these embodiments, the one or more EHR identifiers can further include a hash value. Then, the second EHR system can be configured to authenticate the user associated with the EHR-user identifier based on the EHR-user identifier and the hash value in the EHR report. In more particular of these embodiments, the one or more EHR identifiers can further include a timestamp indicating a reporting time for the EHR report. Then, the second EHR system can be configured to authenticate the user associated with the EHR-user identifier based on the EHR-user identifier and the hash value in the EHR report only within a predetermined amount of time of the reporting time.

In other more particular of these embodiments, the one or more EHR identifiers can include a time stamp. Then, the second EHR system can be configured to calculate the hash value using a hash function operating on hashing data, where the hashing data includes at least one EHR identifier of the one or more identifiers and the time stamp. In still other more particular of these embodiments, the one or more EHR identifiers can further include a computing-device identifier identifying a computing device. Then, the second EHR system can be configured to authenticate the user associated with the EHR-user identifier based on the EHR-user identifier only when the EHR report is sent from the computing device identified by the computing-device identifier.

In even other embodiments, the second EHR system can access information based on the EHR-user identifier and/or the EHR-patient identifier by at least: locating the record for the patient on the second EHR system using the EHR-patient identifier from the EHR report; and accessing the located record for the patient.

FIG. 2 is a flowchart of method 200, in accordance with an example embodiment. Method 200 can be executed by one or more computing devices acting as one or more EHR systems. The computing device can have one or more processors and a non-transient computer readable memory, configured to store executable instructions that, upon execution by the one or more processors, cause the computing device to perform functions. An example computing device is described as computing device 1100 discussed below at least in the context of FIG. 11.

Method 200 can begin at block 210, where an EHR system can receive an EHR report. The EHR report can include one or more EHR identifiers. The one or more EHR identifiers can include an EHR-user identifier, an EHR-patient identifier, and a behavior identifier.

In some embodiments, receiving the EHR report can include determining whether the EHR-user identifier identifies a new user. In response to determining that the EHR-user identifier identifies a new user, the EHR system can add a user to the EHR system, where the added user is identified by the EHR-user identifier.

In other embodiments, receiving the EHR report can include determining whether the EHR-user identifier identifies a new patient. In response to determining that the EHR-patient identifier identifies a new patient, the EHR system can add a patient to the EHR system, where the added patient is identified by the EHR-patient identifier.

At block 220, the EHR system can access information based on the EHR-user identifier and/or the EHR-patient identifier.

At block 230, the EHR system generating an output based on the accessed information. In some embodiments, the EHR-patient identifier can identify a patient being discharged from a medical facility. In particular of these embodiments, the output can include one or more discharge instructions for the patient being discharged. In other embodiments, the output can include a display of radiological information for a patient identified by the EHR-patient identifier.

At block 240, the EHR system can provide the output. In some embodiments, the EHR system can include a display device. Then, providing the output can include providing the output using the display device. In other embodiments, providing the output can include providing the output based on the behavior identifier.

In some embodiments, the EHR system is configured to authenticate users before using the EHR system. In particular of these embodiments, method 200 can include authenticating a user to use the EHR system based on the EHR-user identifier received in the EHR report. In other particular of these embodiments, the one or more EHR identifiers can also include a hash value. Then, authenticating the user to use the EHR system based on the EHR-user identifier can include authenticating the user to use the EHR system based on the EHR-user identifier and the hash value in the EHR report. In other more particular of these embodiments, the one or more EHR identifiers can also include a timestamp indicating a reporting time for the EHR report. Then, authenticating the user to use the EHR system based on the EHR-user identifier and the hash value can include authenticating the user to use the EHR system based on the EHR-user identifier and the hash value only within a predetermined amount of time of the reporting time.

In other more particular of these embodiments, the one or more EHR identifiers can include a time stamp. Then, the EHR system can be configured to calculate the hash value using a hash function operating on hashing data, where the hashing data includes at least one EHR identifier of the one or more identifiers and the time stamp. In still other particular of these embodiments, the one or more EHR identifiers can also include a computing-device identifier identifying a computing device. Then, authenticating the user to use the EHR system based on the EHR-user identifier can include authenticating the user associated with the EHR-user identifier based on the EHR-user identifier only when the EHR report is sent from the computing device identified by the computing-device identifier.

In yet other embodiments, the EHR system can be configured to store a record for a patient identified by the EHR-patient identifier. In particular of these embodiments, the EHR system can access information based on the EHR-user identifier and/or the EHR-patient identifier by at least: locating the record for the patient on the EHR system using the EHR-patient identifier from the EHR report; and accessing the located record for the patient.

Providing Secure and Seamless Authenticated Workflow Between EHR Systems

Figure 3:
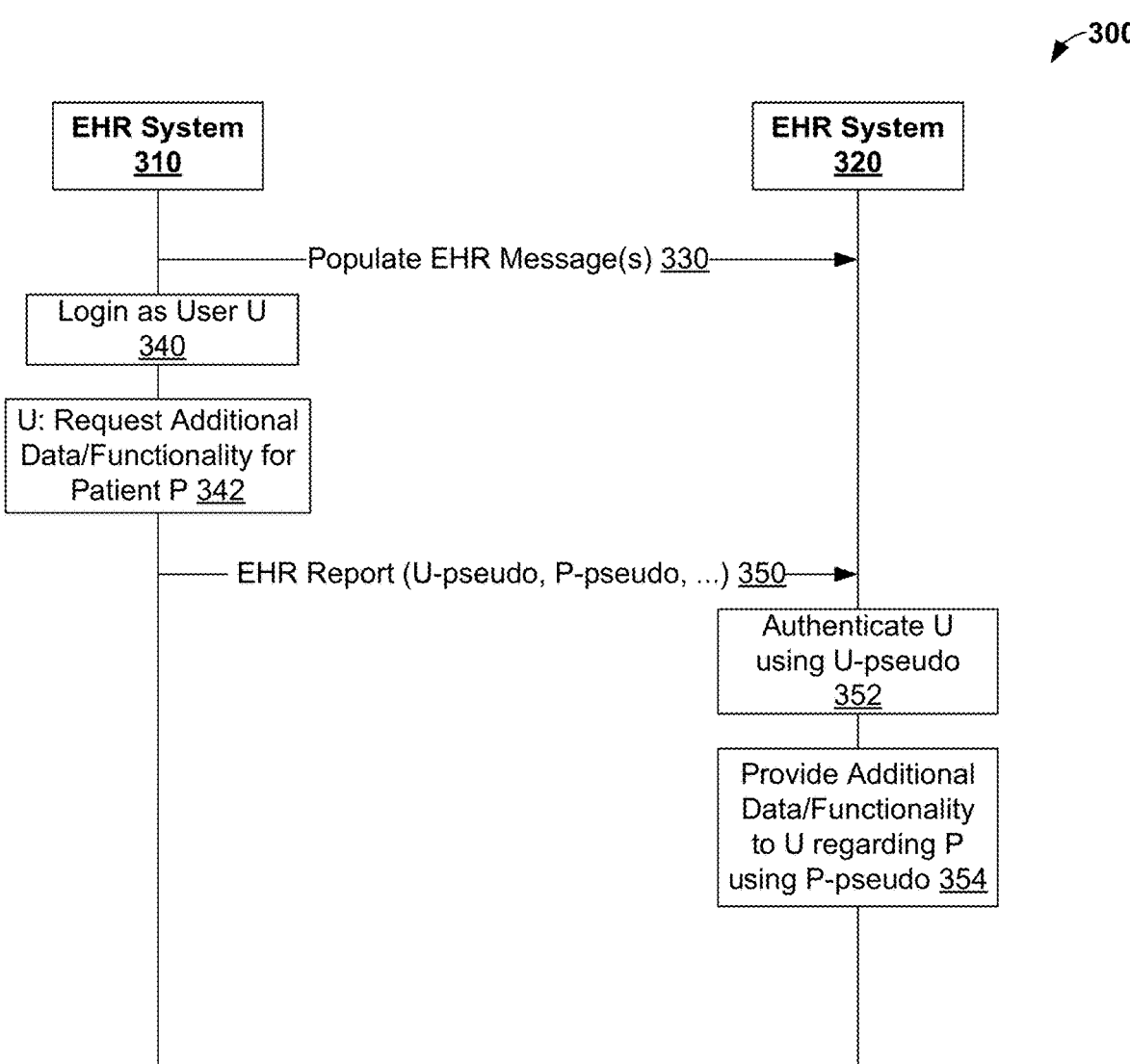
FIG. 3 depicts a scenario where a second EHR system provides additional data and/or functionality for a first EHR system, in accordance with an example embodiment.

FIG. 3 depicts scenario 300 where second EHR system 320 provides additional data and/or functionality for a first EHR system 310, in accordance with an example embodiment.

Prior to scenario 300, both EHR system 310 and 320 have established matching user and patient pseudonyms for both a user U and a patient P. Note that the matching user pseudonym may or may not be a login/user identifier, password, or other identifier. For example, user U may have a user name of "user1234" and a password of "xkis$57!op" for EHR system 310, a user name of "user27", a password of "my newpassword!" for EHR system 320, and a pseudonym of "shared user56" known to both EHR systems 310 and 320.

In some cases, other shared information can be established. For example, EHR systems 310 and 320 both can be configured to share behavior identifiers and/or other context-related pseudonyms for specialized functions of EHR system 320. In scenario 300, EHR system 320 is a patient discharge EHR system, and the behavior identifiers and/or other context-related pseudonyms can specify discharge related functions, such as 'Create Discharge Information" or "Retrieve Discharge Document Created". Many other examples of user names, passwords, and pseudonyms are possible as well.

At the onset of scenario 300, EHRs for a patient P are shared via populate EHR message(s) 330; e.g., using the HL7 protocol. In alternative scenarios to scenario 300, a user pseudonym for user U and/or a patient pseudonym for patient P can be shared via populate EHR message(s) 330 and/or EHR report 350. FIG. 3 shows that scenario 300 continues with user U being authenticated to use EHR system 310 via login 340 to record health information electronically for patient P. At the time of login 340, EHR system 320 is not being used by user U.

At 342 of scenario 300, user U requests EHR system 320 to provide additional functionality and/or data not provided by EHR system 310; e.g., user U is recording the discharge of patient P from a medical facility and requests EHR system 320 to provide discharge instructions for patient P. User U can instruct EHR system 310 to request functionality of EHR system 320; e.g., by use of a command, graphical user interface (GUI) operation (e.g., clicking/pressing on a button, double-clicking on an icon representing EHR system 320), vocal command, gesture, and/or other techniques.

EHR system 310 can then create an EHR report 350 that includes EHR identifiers including user pseudonym "U-pseudo" and patient pseudonym "P-pseudo". EHR report 350 can include other information as well, such as, but not limited to, other pseudonyms and/or identifiers, timestamps, and hash values. Other pseudonyms and/or identifiers can include a behavior identifier to indicate a desired behavior for EHR system 320. For example, suppose EHR system 320 can provide both patient discharge instructions, as indicated above, and patient pre-admission instructions. Then, EHR system 310 can use two different behavior identifiers in reporting to the EHR system 320: one behavior identifier to request patient discharge instruction functionality and data, and another behavior identifier to request for patient pre-admission instruction functionality and data. As another example, a "machine" identifier can identify a computing device acting as the EHR system 310; e.g., by name, fully qualified domain name (FQDN), Internet Protocol (IP) address, Media Access Control (MAC) address, Universal Resource Locator (URL), etc. Further examples include an application identifier to identify software of EHR system 310 being used at the time that use of EHR system 320 is requested and a site identifier can indicate a location, medical facility name, address, site name, or other data to identify where EHR system 310 is resident. Many other pseudonyms and/or identifiers are possible as well.

In some embodiments, EHR report 350 can include only one EHR identifier. For example, if EHR report 350 includes only user pseudonym "U-pseudo", then EHR system 320 can interpret EHR report 350 as a request to authenticate the user represented by user pseudonym "U-pseudo". As another example, if EHR report 350 includes only patient pseudonym "P-pseudo", then EHR system 320 can interpret EHR report 350 as a request to (a) first authenticate a user and then (b) allow the authenticated user to process EHRs related to the patient represented by patient pseudonym "P-pseudo". Other examples of EHR reports with a single identifier are possible as well.

EHR report 350 can be secured. For example, EHR system 310 can use a hash function to generate a hash value for some or all of the pseudonyms and/or identifiers in EHR report 350 and can then include the hash value as part of EHR report 350. A hash function can include an algorithm that takes hashing data as input and generates a fixed-length hash value as a result. In particular, the hashing data can include one or more pseudonyms and/or identifiers in EHR report 350, and perhaps additional data. Then, upon reception of EHR report 350, EHR system 320 can recalculate the hash value based on the received pseudonyms and/or identifiers. If the recalculated hash value matches the hash value provided in EHR report 350, then the pseudonyms and/or identifiers in EHR report 350 can be determined to be valid by EHR system 320.

In some cases, EHR report 350 can include a timestamp. Then, if EHR system 320 receives the report within a threshold amount of time after a time indicated by the timestamp, EHR system 320 can determine that the report is secure. For example, let the threshold amount of time is 5 seconds, and let the timestamp in EHR report 350 indicate a time of 7:30:00—then, EHR system 320 can determine that EHR report 350 is valid until 7:30:05. However, if the recalculated hash value does not match the hash value in EHR report 350 and/or EHR system 320 receives EHR report 350 after the threshold amount of time, EHR system 320 can determine that the report is insecure and discard the report.

In some embodiments, EHR report 350 can be formatted as a single line that consists of a set of pseudonyms/ identifiers, a timestamp, and a hash value for the pseudonyms and timestamp. In particular embodiments, EHR report 350 can include a user pseudonym identifying a user of EHR system 310; e.g., user U, a patient visit pseudonym identifying a medical session with a patient, a patient pseudonym identifying a patient whose records are processed/stored by EHR system 310; e.g., patient P, a site-identifier pseudonym identifying a location of a patient visit, a time stamp, a machine name, and a hash value for some or all of the pseudonyms, time stamp, and/or machine name. In other embodiments, part or all of EHR report 350 can be encrypted; e.g., some or all of the pseudonyms, time stamp, machine name, and other information in EHR report 350 can be encrypted. In particular embodiments, the hash value can be calculated by use of a hash function operating on hashing data, where the hashing data includes some or all of the EHR identifiers, including pseudonyms, and at least the time stamp, so that a simple change of any data being hashed, including the time stamp, will likely lead to a different hash value.

In still other embodiments, EHR system 310 can have a script or other software to generate EHR report 350. The script or other software can be configured to act as a printer to virtually print, or otherwise provide, EHR report 350 to EHR system 320. Then, EHR system 320 can have a program or other software to accept the (virtually printed) EHR report 350. The program or other software on EHR system 320 can decrypt part or all of EHR report 350 and/or validate EHR report 350 by confirming the hash value is correct.

In even other embodiments, EHR report 350 can include a reference to additional data that is part of the report; e.g., text, binary, image, audio, video, and/or other type(s) of data that is part of the report. For example, EHR report 350 can include at least three data items: the user pseudonym U-pseudo (or other user identification information), the patient pseudonym P-pseudo (or other patient identification information), and a data identifier D-ID. In this example, data identifier D-ID can be a unique value that indicates that data accessed using the reference to additional data is also associated with the user and/or patient identifiers in EHR report 350; e.g., D-ID can be a random value, a generated key value, hash value, or some other unique value. In this example, the reference to additional data can be a name of a predetermined file; e.g., "EHR_file1". The data in the predetermined file can be stored with or without the use of additional file processing, such as hashing, encryption, and/ or compression of part or all of the predetermined file.

Then, upon reception of EHR report 350, EHR system 320 can retrieve U-pseudo, P-pseudo, and D-ID values from EHR report 350, and access the data in the predetermined file. In this example, the first data item in the predetermined file is a copy of the unique value used as the data identifier. If D-ID in EHR report 350 matches the first data item in the predetermined file, then EHR system 320 can determine that the data in the predetermined file is associated with the user associated with U-pseudo and the patient associated with P-pseudo, and continue with scenario 300. If D-ID EHR report 350 does not matches the first data item in the predetermined file, then EHR system 320 can determine that the data in the predetermined file is not associated with the user associated with U-pseudo and the patient associated with P-pseudo, and perhaps end scenario 300 or report an error; e.g., an error associated with data reference D-ID not being associated with U-pseudo and/or P-pseudo.

In some of the even other embodiments, the data identifier D-ID can be part or all of the reference to additional data. For example, suppose D-ID equals a value "abc", then the reference to additional data can be a file whose name is based on the data identifier value D-ID; e.g., file names "abc", "abc.dat", "C:\EHR Reports\abc", etc. As another example, the reference to additional data can be a Uniform Resource Locator (URL) or other identifier whose name is based on the data identifier value D-ID; e.g., URLs "abc", "http: // d/abc", "http: // EHRreps.abchospital.com/abc", "https: // abc", etc. In some cases, such files can be periodically or otherwise deleted; e.g., using a circular file naming strategy such as "EHRfile00", "EHRfile01" . . . "EHRfile99" and then restarting with "EHRfile00". In this fashion, single-threaded or multi-threaded access to references to additional data can be supported.

In yet other of the even other embodiments, the data identifier D-ID and the reference to additional data can be distinct. For example, suppose D-ID equals a value "d137ff" and the reference to additional data is "def". Then file names and/or URLs such as "def", "def.dat", "C:\EHR Reports\def", "http: // d/def", "http: // EHRreps.abchospi-tal.com/def", "https: // EHRreps.defhospital/def", "https: // def", etc. can be used and the data identifier D-ID can be used to verify the additional data obtained via the reference to additional data is associated with U-pseudo and/or P-pseudo; e.g., that a portion or all of the additional data matches, hashes, or otherwise is related to the D-ID value of "d137ff". In still other embodiments, some or all of these embodiments related to EHR report 320 can be combined.

In alternative scenarios to scenario 300, a user pseudonym for user U and/or a patient pseudonym for patient P can be introduced to EHR system 320 via EHR report 350. In these scenarios, EHR system 320 can establish U as a new user of EHR system 320 and/or establish P as a new patient of EHR system 320; e.g., use the user pseudonym as a user identifier to EHR system 320 and/or use the patient pseudonym to locate records for patient P that are managed by EHR system 320, and provide the requested additional data/functionality as permitted by authorization(s) granted by EHR system 320 to new user U and/or related to new patient P.

Then, at 352, the program can confirm that pseudonym U-pseudo is valid for EHR system 320 and so authenticate user U to use EHR system 320. After determining that user U is authenticated, the program can instruct other software and/or hardware of EHR system 320 to provide data and/or functionality 354 not available using EHR system 310 on behalf of patient P.

Note that if pseudonyms and/or identifiers in EHR report 350 are valid, user U's context is extended from EHR system 310 to EHR system 320 without specific user intervention. That is, user U did not have to login or otherwise be authenticated to use EHR system 320. Further, user U did not enter or otherwise provide any additional information to EHR system 320 to have EHR system 320 provide data and/or functionality for patient P. So, upon making request 342, user U is authenticated to EHR system 320 and can continue working on patient P's records automatically. After EHR system 320 provides data and/or functionality not available using EHR system 310 at 354, scenario 300 can end.

In other scenarios, multiple EHR reports can be received by EHR system 320. For example, a first EHR report can introduce a user U1 to EHR system 320 to process records for a patient P1 known to EHR system 320, where the processing is guided by a behavior identifier passed in first EHR report. In this example, behavior identifiers include a B1 identifier to add a patient record for P1, a B2 identifier to retrieve the patient record for P1, a B3 identifier to update the patient record for P1, a B4 identifier to delete the patient record for P1, a B5 identifier to retrieve all patient records associated with user U1, and a B6 identifier to retrieve all patient records. If the first EHR report includes a B2 identifier, then EHR system 320 can retrieve the patient record for P1 and perhaps display, present, or otherwise provide the retrieved record.

Later, a second EHR report can be received by EHR system 320 with a user pseudonym for user U1, a patient pseudonym for patient P1, and a B3 identifier. In response to the second EHR report, EHR system 320 can retrieve the patient record for P1 and make the retrieved patient record for P1 available for updating; e.g., provide a user interface to update the patient record, accept changes to the patient record via the user interface, and then save the changed patient records. Even later, a third EHR report can be received by EHR system 320 with only a B6 behavior identifier. In response to the third EHR report, EHR system 320 can retrieve all patient records and perhaps display, present, or otherwise provide the retrieved records. Many other examples are possible as well.

Figure 4:
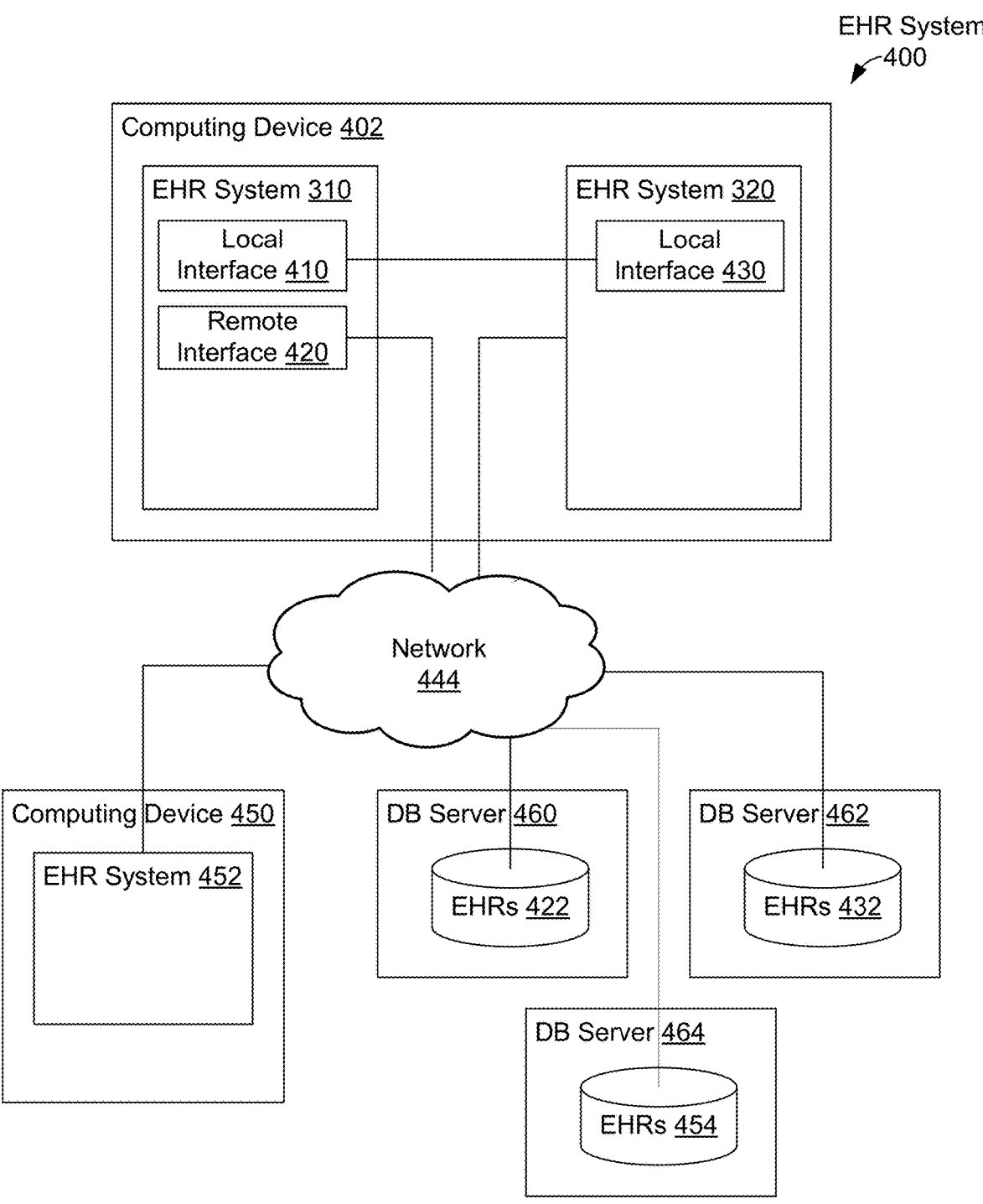
FIG. 4 depict a networked EHR system, in accordance with an example embodiment

FIG. 4 depicts networked EHR system 400 connected using network 444, in accordance with an example embodiment. Network 444 can be a network such as network 1006 discussed below in the context of FIG. 10.

Network 444 can connect computing device 402, computing device 450, and database (DB) servers 460, 462, and 464 as shown in FIG. 4. Computing device 402 can include, and can be configured with hardware and/or software at least to act as two EHR systems: EHR system 310 and EHR system 320. EHR system 310 can include local interface 410 and remote interface 420. Electronic health records used by EHR system 310 can be stored remotely; e.g., resident on a dedicated database server 460 as EHRs 422. EHR system 320 includes local interface 430. Electronic health records used by EHR system 320 can be stored remotely; e.g., resident on a dedicated database server 462 as EHRs 432.

Computing device 450 can include EHR system 452. In some embodiments, EHR 454 can include a local interface and/or a remote interface. Electronic health records used by EHR system 452 can be stored remotely; e.g., resident on a dedicated database server 464 as EHRs 454. Each of database servers 460, 462, 464 can be a computing device configured to store respective EHRs 422, 432, 454 and to perform database operations related to the respective EHRs; e.g., receive queries for the respective EHRs via network 444, retrieve none, some, or all respective EHRs based on the received queries, and communicate any retrieved EHRs via network 444.

In some embodiments, EHR system 400 can omit database servers 460, 462, and 464; e.g., by storing EHRs locally within EHR systems 310, 320, and/or 452. In other embodiments, some or all of database servers 460, 462, and 464 and respective EHRs 422, 432, and 454 can be combined onto fewer servers; e.g., one database server can store and process all of EHRs 422, 432, and 454.

Figure 5:
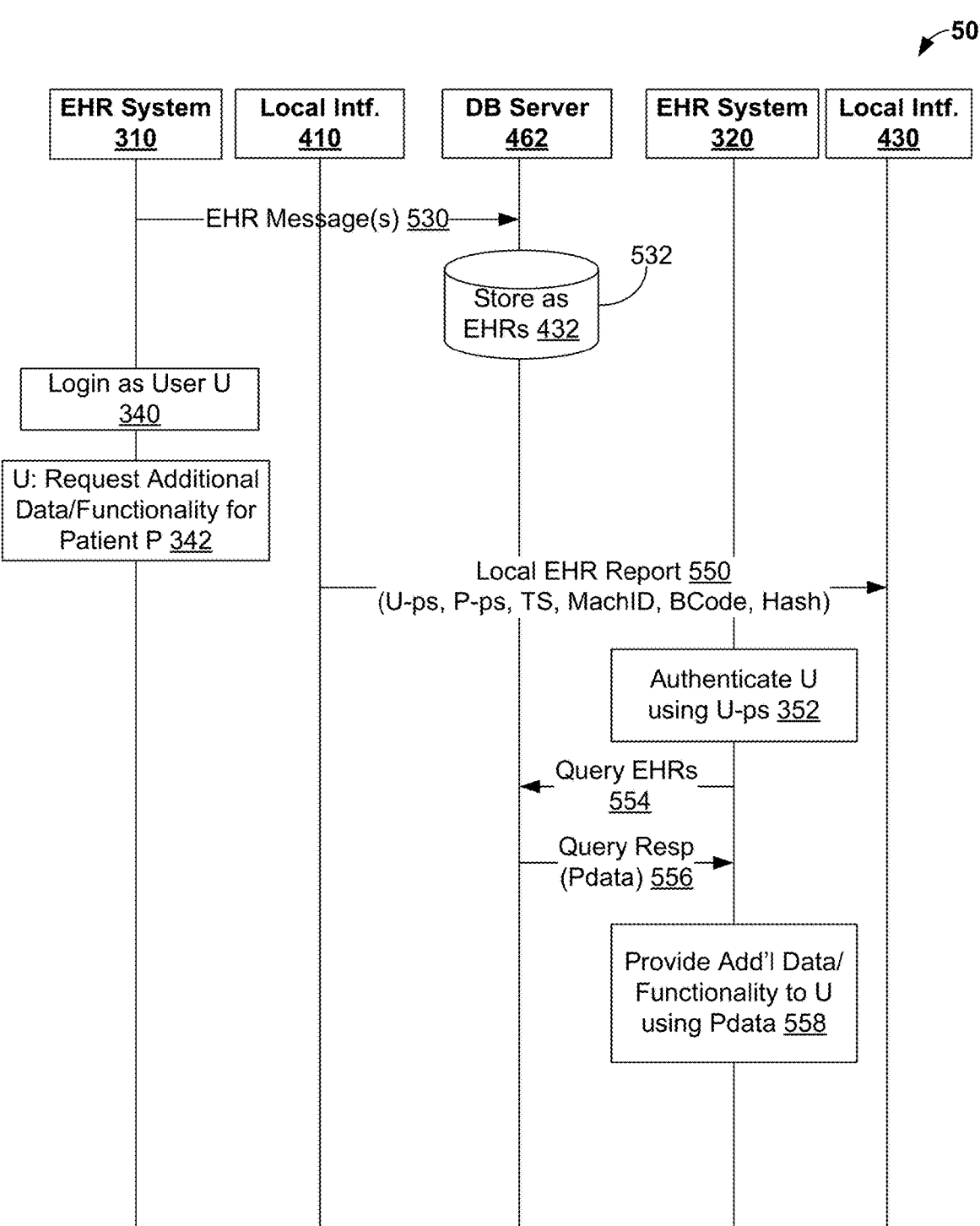
FIG. 5 depicts a scenario within the networked EHR system of FIG. 4 where a second EHR system provides additional data and/or functionality for a first EHR system, in accordance with an example embodiment.

FIG. 5 depicts scenario 500 within network EHR system 400 where EHR system 320 provides additional data and/or functionality for EHR system 310, in accordance with an example embodiment. For example, EHR system 320 can act as a thick client for EHR system 310.

Prior to scenario 500, both EHR systems 310 and 320 have established matching user and patient pseudonyms for both a user U and a patient P. Further, in scenario 500, at least patient visit pseudonyms identifying medical sessions with patients, including patient P, site-identifier pseudonyms, and behavior identifiers have been established for both EHR systems 310 and 320.

At the onset of scenario 500, EHRs for patient P are shared via EHR message(s) 530 with data base server 462; e.g., using the HL7 protocol. In alternative scenarios to scenario 500, a user pseudonym for user U and/or a patient pseudonym for patient P can be shared after the onset of scenario 500; e.g., via populate EHR message(s) 530 and/or local EHR report 550.

At 532, data base server 462 then stores EHRs conveyed in EHR message(s) 530 as EHRs 432. In some embodiments not shown in FIG. 5, EHR message(s) 530 can be communicated to one or more other or additional database servers.

FIG. 5 shows that scenario 500 continues with user U being authenticated to use EHR system 310 via login 340, as discussed in the context of scenario 300 and FIG. 3. Scenario 500 continues at 342 with user U requesting additional functionality and/or data not provided by EHR system 310 to be provided by EHR system 320, such as discussed in the context of scenario 300 and FIG. 3.

Scenario 500 continues with EHR system 310 creating EHR report 550, which includes user pseudonym "U-ps", patient pseudonym "P-ps", time stamp TS, machine identifier MachID, behavior identifier BCode, and hash value Hash. User pseudonyms, patient pseudonyms, time stamps, machine identifiers, behavior identifiers, and hash values are discussed above in the context of at least FIG. 3. EHR report 550 can include other information as well, such as, but not limited to, other pseudonyms and/or identifiers; e.g., patient visit and pseudonyms, such as discussed above in the context of at least FIGS. 3 and 5. EHR report 550 can be secured using at least hash value Hash and timestamp TS, as discussed above in the context of EHR report 350 discussed above in the context of FIG. 3.

In some embodiments, EHR report 550 can be formatted as a single line as discussed above in the context of at least FIG. 3. In still other embodiments, EHR system 310 can have a script or other software to generate EHR report 550, as discussed above in the context of FIG. 3. Then, EHR system 320 can have a program or other software to accept, validate, and perhaps decrypt EHR report 550, such as discussed above in the context of FIG. 3.

In some embodiments, such as shown in FIG. 4, EHR systems 310 and 320 are resident on the same computing device; e.g., computing device 400. In these embodiments, EHR system 310 can communicate EHR report 550 to EHR system 320 via memory transfer. Further, in these embodiments, as EHR report 550 is communicated by memory transfers, which are typically relatively quick, the threshold amount of time for validating EHR reports discussed in the context of FIG. 3 can be relatively short; e.g., one second or less.

In alternative scenarios to scenario 500, a user pseudonym for user U and/or a patient pseudonym for patient P can be introduced to EHR system 320 via EHR report 550. In these scenarios, EHR system 320 can establish U as a new user of EHR system 320 and/or establish P as a new patient of EHR system 320; e.g., use the user pseudonym as a user identifier to EHR system 320 and/or use the patient pseudonym to locate records for patient P that are managed by EHR system 320, and provide the requested additional data/functionality as permitted by authorization(s) granted by EHR system 320 to new user U and/or related to new patient P.

Scenario 500 can continue at 352, where EHR system 320 can confirm that pseudonym U-ps is valid for EHR system 320 and so authenticate user U to use EHR system 320, such as discussed above in the context of FIG. 3.

Scenario 500 continues with EHR system 320 generating and sending query EHRs message 554 to database server 462. For example, query EHRs message 554 can include a database query for data related to the patient identified via patient pseudonym P-ps. The database query and/or query EHRs message 554 can be formatted as indicated using a database query language, such but not limited to the Structured Query Language (SQL). In some embodiments not shown in FIG. 5, query EHRs message 554 can be sent to one or more other or additional database servers.

In response to query EHRs message 554, database server 462 can search for data related to query EHRs message 554. Upon finding related data, database server 462 can provide the related data as part of a query response, such as the Pdata (patient data) shown as part of query response message 556 in FIG. 5. Pdata can include, but is not limited to, textual, audio, video, image, and/or binary data. At 558 of scenario 500, FIG. 5 shows that EHR system 320 can provide data, such as part or all of Pdata, and/or functionality not available using EHR system 310 on behalf of patient P. After EHR system 320 provides data and/or functionality not available using EHR system 310 at 558, scenario 500 can end.

In other scenarios not shown in FIG. 5, EHR system 320 may communicate with one or more other or additional database servers and perhaps other computing devices to obtain Pdata; e.g., database server 460 for storing EHRs 422 related to EHR 310. In still other scenarios, multiple EHR reports can be received by EHR system 320, such as discussed above in the context of FIG. 3.

Figure 6:
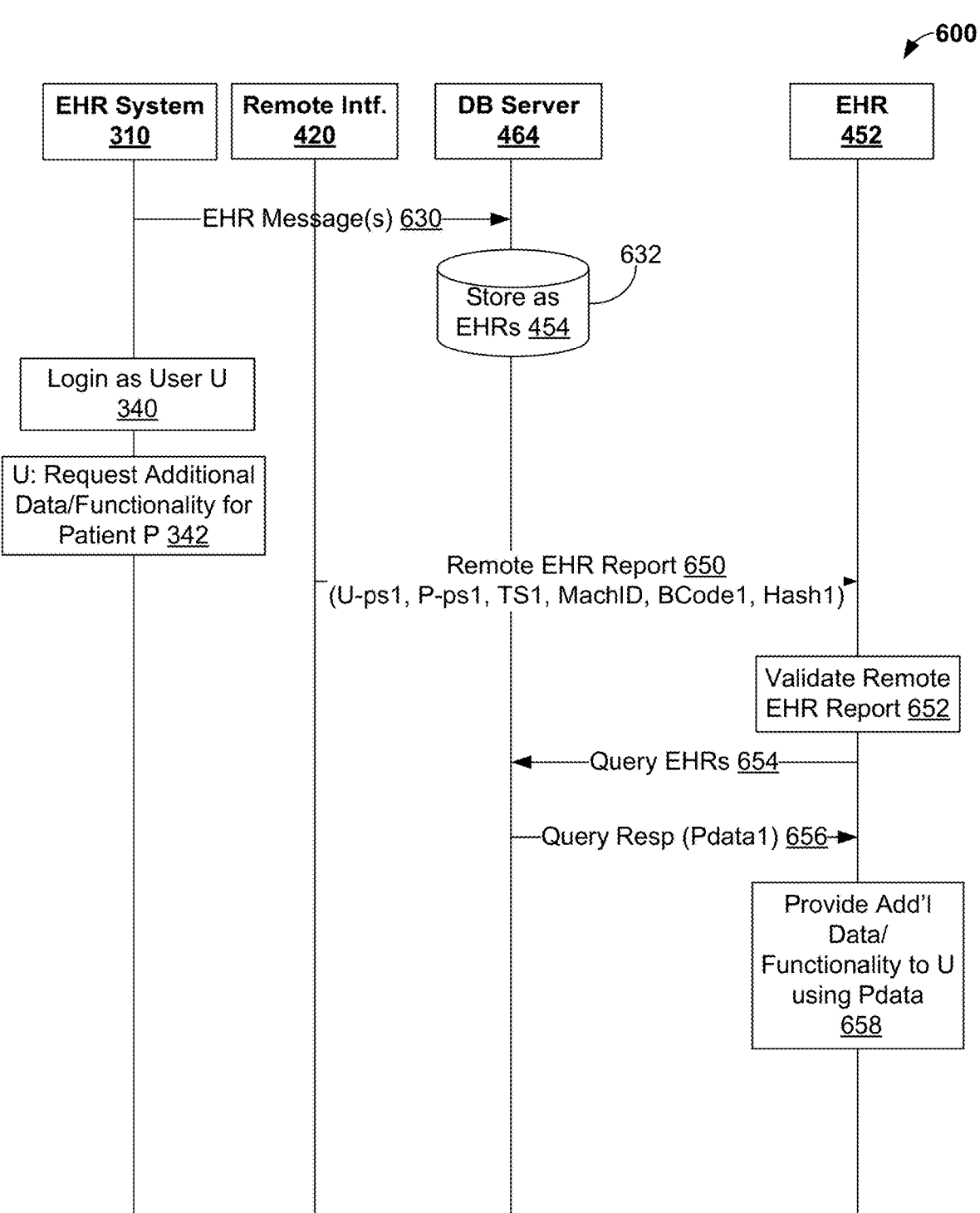
FIG. 6 depicts another scenario within the networked EHR system of FIG. 4 where a second EHR system provides additional data and/or functionality for a first EHR system, in accordance with an example embodiment.

FIG. 6 depicts scenario 600 within network EHR system 400 where EHR system 452 provides additional data and/or functionality for EHR system 310, in accordance with an example embodiment. For example, EHR system 452 can act as a thin web client for EHR system 310.

Prior to scenario 600, both EHR systems 310 and 452 have established matching user and patient pseudonyms for both a user U and a patient P. Further, in scenario 500, at least patient visit pseudonyms identifying medical sessions with patients, including patient P, site-identifier pseudonyms, and behavior identifiers have been established for both EHR systems 310 and 452.

At the onset of scenario 600, EHRs for patient P are shared via EHR message(s) 630 with data base server 464; e.g., using the HL7 protocol. In alternative scenarios to scenario 600, a user pseudonym for user U and/or a patient pseudonym for patient P can be shared after the onset of scenario 500; e.g., via populate EHR message(s) 630 and/or remote EHR report 650.

At 632, data base server 464 then stores EHRs conveyed in EHR message(s) 630 as EHRs 454. In some embodiments not shown in FIG. 5, EHR message(s) 630 can be communicated to one or more other or additional database servers.

FIG. 6 shows that scenario 600 continues with user U being authenticated to use EHR system 310 via login 340, as discussed in the context of scenarios 300 and 500 and respective FIGS. 3 and 5. Scenario 600 continues at 342 with user U requesting additional functionality and/or data not provided by EHR system 310 to be provided by EHR system 452, such as discussed in the context of scenarios 300 and 500 and respective FIGS. 3 and 5.

Scenario 600 continues with EHR system 310 creating EHR report 650, which includes user pseudonym "U-ps1", patient pseudonym "P-ps1", time stamp TS1, machine identifier MachID, behavior identifier BCode1, and hash value Hash1. User pseudonyms, patient pseudonyms, time stamps, machine identifiers, behavior identifiers, and hash values are discussed above in the context of at least FIGS. 3 and 5. EHR report 650 can include other information as well, such as, but not limited to, other pseudonyms and/or identifiers; e.g., patient visit and pseudonyms, such as discussed above in the context of at least FIGS. 3 and 5. EHR report 650 can be secured using at least hash value Hash1 and timestamp TS1, such as discussed above in the context of EHR reports 350 and 550 discussed above in the context of respective FIGS. 3 and 5.

In some embodiments, EHR report 650 can be formatted as a single line as discussed above in the context of at least FIGS. 3 and 5. In still other embodiments, EHR system 310 can have a script or other software to generate EHR report 650, as discussed above in the context of FIGS. 3 and 5. Then, EHR system 452 can have a program or other software to accept, validate, and perhaps decrypt EHR report 650, such as discussed above in the context of FIGS. 3 and 5.

In some embodiments, such as shown in FIG. 4, EHR systems 310 and 452 are not resident on the same computing device; e.g., EHR system 310 is resident on computing device 400 and EHR system 452 is resident on computing device 450. In these embodiments, EHR system 310 can communicate EHR report 650 to EHR system 320 via a network; e.g., network 444.

In alternative scenarios to scenario 600, a user pseudonym for user U and/or a patient pseudonym for patient P can be introduced to EHR system 452 via EHR report 550. In these scenarios, EHR system 452 can establish U as a new user of EHR system 452 and/or establish P as a new patient of EHR system 452 e.g., use the user pseudonym as a user identifier to EHR system 452 and/or use the patient pseudonym to locate records for patient P that are managed by EHR system 452, and provide the requested additional data/functionality as permitted by authorization(s) granted by EHR system 452 to new user U and/or related to new patient P.

Scenario 600 can continue at 652, where EHR system 452 can confirm that pseudonym U-ps1 is valid for EHR system 452 and so authenticate user U to use EHR system 452, such as discussed above in the context of FIGS. 3 and 5.

Scenario 600 continues with EHR system 320 generating and sending query EHRs message 654 to database server 464. For example, query EHRs message 654 can include a database query for data related to the patient identified via patient pseudonym P-ps1. The database query and/or query EHRs message 654 can be formatted as indicated using a database query language, such but not limited to SQL. In some embodiments not shown in FIG. 5, query EHRs message 654 can be sent to one or more other or additional database servers.

In response to query EHRs message 654, database server 464 can search for data related to query EHRs message 654. Upon finding related data, database server 464 can provide the related data as part of a query response, such as the Pdata1 shown as part of query response message 656 in FIG. 6. Pdata1 can include, but is not limited to, textual, audio, video, image, and/or binary data. At 658 of scenario 600, FIG. 6 shows that EHR system 452 can provide data, such as part or all of Pdata, and/or functionality not available using EHR system 310 on behalf of patient P. After EHR system 452 provides data and/or functionality not available using EHR system 310 at 658, scenario 600 can end.

In some embodiments, EHR system 452 can provide the additional data and/or functionality via additional software; e.g., using a browser or other software configured to display information that may be communicated via a network, such as network 444. In other embodiments, the functionality of EHR systems 320 and 452 can be combined.

In other scenarios not shown in FIG. 6, EHR system 452 may communicate with one or more other or additional database servers and perhaps other computing devices to obtain Pdata; e.g., database server 460 for storing EHRs 422 related to EHR 310. In still other scenarios, multiple EHR reports can be received by EHR system 452, such as discussed above in the context of FIG. 3.

Figure 8:
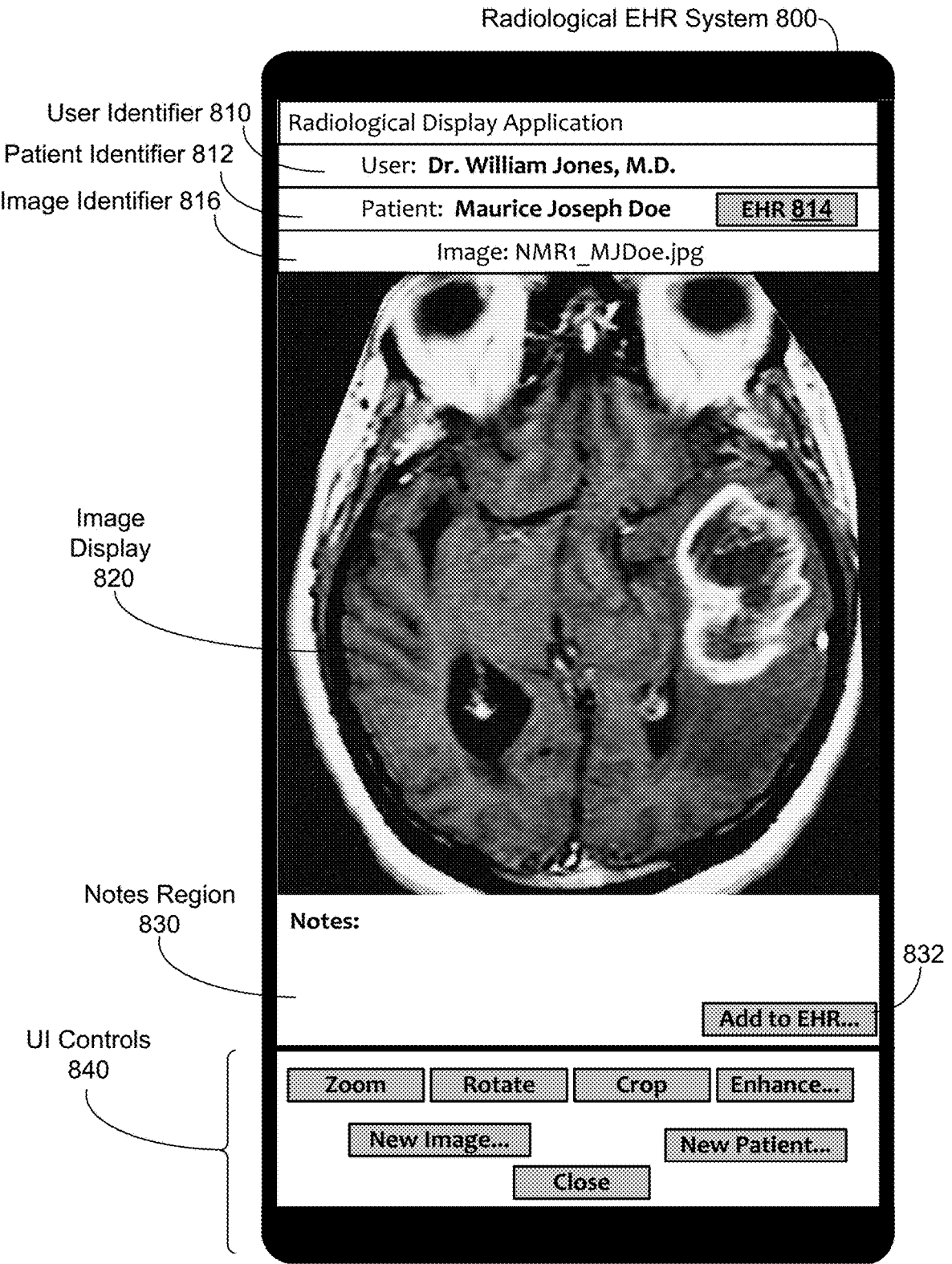
FIG. 8 depicts a user interface for a radiological EHR system, in accordance with an example embodiment.
Figure 9:
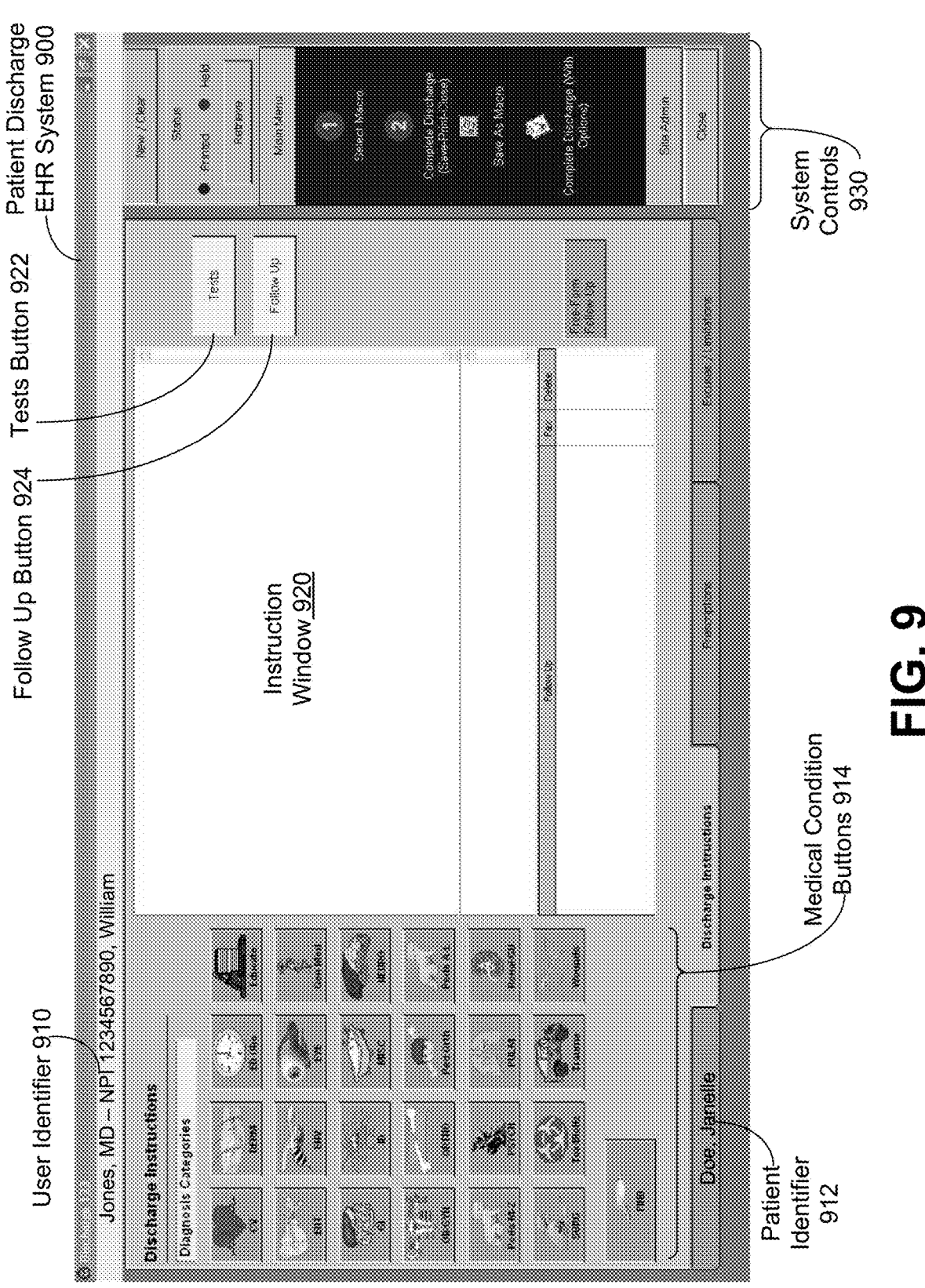
FIG. 9 depicts a user interface for a patient discharge EHR system, in accordance with an example embodiment.

As indicated above, the second EHR systems; e.g., EHR system 320 of FIGS. 3-5 and EHR system 452 of FIGS. 4 and 6, can provide data and/or functionality that cannot be provided by the first EHR system; e.g., EHR system 310 of FIGS. 3-6. In some cases, as mentioned above, the first EHR system can be a text-based system. For these cases, FIGS. 7-9 show examples of second EHR systems that can provide data and/or functionality that the text-based first EHR system cannot provide.

FIG. 7 shows scenario 700 for using user interface 712 to a first EHR system; e.g., EHR system 310 and user interface 720 to a second EHR system; e.g., EHR system 320 or 452.

Scenario 700 begins with window 710 displaying first EHR system user interface 712, as shown in the upper portion of FIG. 7. Window 710 can be part of a GUI for a computing device configured to communicate with both the first and second EHR systems; e.g., computing device 1000. Window 710 includes a smaller window for first EHR system user interface 712. In scenario 700, the first EHR system maintains health records for a hospital HOSP using a text-oriented EHR system (TOEHR) shown in user interface 712 as "TOEHR SYSTEM".

First EHR system user interface 712 indicates that a user "WJONES" is reviewing a "Patient Record" for a patient named "Mary Q. Doe". User interface 712 offers the user a menu of choices from "01—Biographical Information" to "08—Discharge (external)". The label "(external)" in the menu of choices indicates functionality provided by a second EHR system that is separate from the first EHR system.

In scenario 700, the user selects option "06" for "Clinical Records/Archive (external)" of the menu of choices provided by user interface 712. In scenario 700, the second EHR system includes a clinical records/archive system for a clinic CL1 unaffiliated with the hospital HOSP. The second EHR system can have access to data, such as medical records for clinic CL1, which are inaccessible to the first EHR system, and can provide functionality, such as EKG chart review, not provided by the first EHR system.

In response, the first EHR system generates an EHR report that includes two or more EHR identifiers—the EHR identifiers include a user pseudonym for user WJONES and a patient pseudonym for patient MARY Q. DOE. In some scenarios, the EHR report also includes other EHR identifiers, a hash value and/or a time stamp, as discussed above. Once generated, the first EHR system communicates the EHR report to the second EHR system, as discussed above in the context of at least FIGS. 3, 5, and 6.

In scenario 700, the second EHR system uses the pseudonym for user WJONES in the EHR report to authenticate Dr. Jones without additional user data entry; i.e., the second EHR system uses the user pseudonym to authenticate the user automatically. In scenario 700, the second EHR system also uses the patient pseudonym for MARY Q. DOE in the EHR report to locate Ms. Doe's records in the second EHR system without additional user data entry; i.e., the second EHR system uses the patient pseudonym to locate the patient's records automatically.

In response to receiving the EHR report and processing the pseudonyms as indicated in the paragraph above, the second EHR system can generate second EHR system user interface 720 for display on window 710. FIG. 7 shows that second EHR system user interface 720 is being used by a user "Bill Jones, M.D." for patient "Mary Q. Doe".

Additionally, FIG. 7 shows that second EHR system user interface 720 includes an electrocardiogram (EKG) chart button, an electroencephalogram (EEG) chart button, a "full chart" button to access textual, audio, video, image, and/or other types of records related to a patient, a tests button to schedule tests for the patient, an appointments button to schedule appointments for the patient, a visit history to show a summary of previous visits by the patient, a new script button to enable the user to write a prescription for the patient, and a notes button for the user to make notes and/or amend the full chart. Second EHR system user interface 720 further includes buttons to select a new patient, export medical records to another system, import medical records from another system, and exit the user interface. In other embodiments, second EHR system user interface 720 can have more, fewer, and/or different controls; e.g., buttons.

In scenario 700, the EKG button is shown in grey to indicate user selection. In response, the second EHR system generates and displays chart 722, which shows EKG results for the patient. In scenario 700, after chart 722 is displayed, the user selects the exit button to exit user interface 720, and the window used to display user interface 722 can be closed. After the exit button is selected, window 710 reverts to the display as indicated at upper portion of FIG. 7, and scenario 700 can end.

FIG. 8 depicts a user interface for radiological EHR system 800, in accordance with an example embodiment. Radiological EHR system 800, acting as a second EHR system; e.g., EHR system 320 or 452, can provide both data and functionality that cannot be provided by a text-based first EHR system. The additional data can include, for example, radiological data, and the additional functionality can include, for example, display of images related to the radiological data.

FIG. 8 shows that a user interface to radiological EHR system 800 includes user identifier display 810 for a user "Dr. William Jones, M.D.", patient identifier 812 for a patient "Maurice Joseph Doe", EHR button 814 for providing additional EHR records (e.g., charts, biographical information) for the patient, and image identifier 816 for an image "NMR1_MJDoe.jpg" being displayed by the user interface. The image "NMR1_MJDoe.jpg" is displayed in image display 820.

Additional EHRs can be generated using the user interface to radiological EHR system 800 shown in FIG. 8. For example, notes region 830 can be used to generate notes about the patient and/or the image. The notes can be added to the EHRs managed, and perhaps stored, by radiological EHR system 800 using add to EHRs button 832.

User interface (UI) controls 840 can be used to manipulate the displayed image, such as by zooming in or out (i.e., enlarging or shrinking), rotating, cropping, and enhancing an image displayed in image display 820. UI controls 840 can also be used to select a new image and/or a new patient, and to close the user interface for radiological EHR system 800. Other user interfaces and user interface controls are possible as well. FIG. 8 shows close the user interface for radiological EHR system 800 displayed using a portable computing device; e.g., a smart phone or tablet computer. In other cases, the user interface for radiological EHR system 800 can be displayed using other types of computing devices configured to display graphical user interfaces (GUIs); e.g., a desktop computer, a laptop computer.

FIG. 9 depicts a user interface for patient discharge EHR system 900, in accordance with an example embodiment. Patient discharge EHR system 900, acting as a second EHR system; e.g., EHR system 310 or 452, can provide both data and functionality that cannot be provided by a text-based first EHR system. The additional data can include, for example, patient discharge instructions, and the additional functionality can include, for example, display of patient discharge instructions and presentation of sounds and/or images related to patient discharge instructions.

FIG. 9 shows that a user interface to patient discharge EHR system 900 includes user identifier display 910 for a user "Jones, MD—NPI 1234567890, William", patient identifier 912 for a patient "Doe, Janelle", medical condition buttons 914 for generating discharge instructions for the patient, instruction window 920 for displaying discharge instructions, and perhaps other EHRs, tests button 922 to add and/or request tests to discharge instructions, and follow up button 924 to add and/or schedule follow-up visits with medical practitioner(s)/medical facilities for the patient. System controls 930 can be used to create new discharge instructions, clear/erase discharge instructions being generated, to display a status of discharge instructions, to provide a main menu for patient discharge EHR system 900, to access site administrator functionality, and to close the user interface to patient discharge EHR system 900.

Other user interfaces and user interface controls to patient discharge EHR system 900 are possible as well. FIG. 9 shows close the user interface for patient discharge EHR system 900 displayed using a window of a GUI for a computing device such as a desktop computer or a laptop computer. In other cases, the user interface for patient discharge EHR system 900 can be displayed using other types of computing devices; e.g., a smart phone, a tablet computer.

Example Data Network

Figure 10:
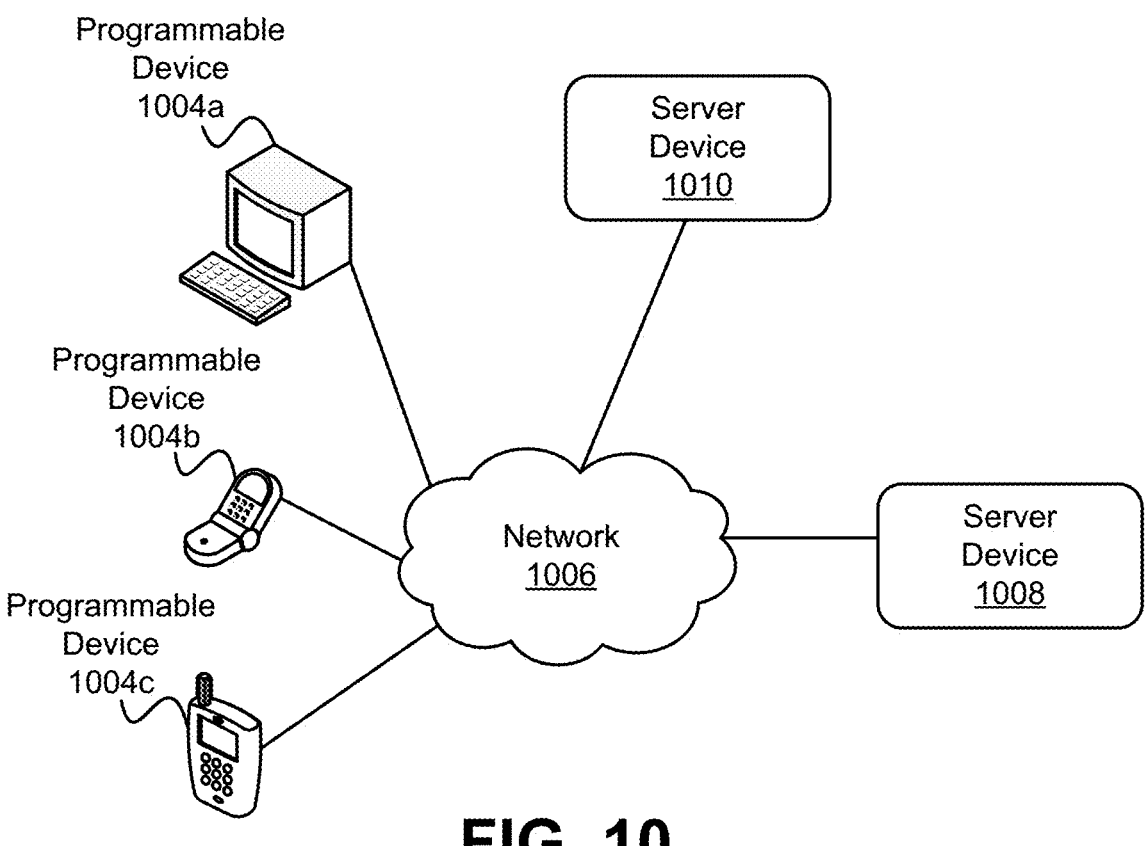
FIG. 10 depicts a distributed computing architecture, in accordance with an example embodiment.

FIG. 10 shows server devices 1008, 1010 configured to communicate, via network 1006, with programmable devices 1004a, 1004b, and 1004c. Network 1006 may correspond to the public Internet, a wide area network (WAN), local area network (LAN), a corporate intranet, or any other type of network configured to provide a communications path between networked computing devices. The network 1006 may also correspond to a combination of one or more LANs, WANs, corporate intranets, and/or the public Internet.

Although FIG. 10 only shows three programmable devices, distributed application architectures may serve larger or smaller numbers of programmable devices. Moreover, programmable devices 1004a, 1004b, and 1004c (or any additional programmable devices) may be any sort of computing device, such as a laptop computer, desktop computer, smart appliance, wearable computing device, network terminal, wireless communication device (e.g., a cell phone or smart phone), and so on. In some embodiments, some or all of programmable devices 1004a, 1004b, and 1004c can be configured to perform some or all of the herein-described functionality of a computing device.

Server devices 1008, 1010 can be configured to perform one or more services, as requested by programmable devices 1004a, 1004b, and/or 1004c. For example, server device 1008 and/or 1010 can provide content to programmable devices 1004a-1004c. The content can include, but is not limited to, medical records, web pages, hypertext, scripts, binary data such as compiled software, images, audio, and/or video. The content can be compressed and/or uncompressed and can be encrypted and/or unencrypted. Other types of content are possible as well. As another example, server device 1008 and/or 1010 can provide programmable devices 1004a-1004c with access to data and/or software for health-related, graphical, audio, video, World Wide Web/Internet utilization, database, search, computation, and/or other functions. Many other examples of server devices are possible as well.

Computing Device Architecture

Figure 11:
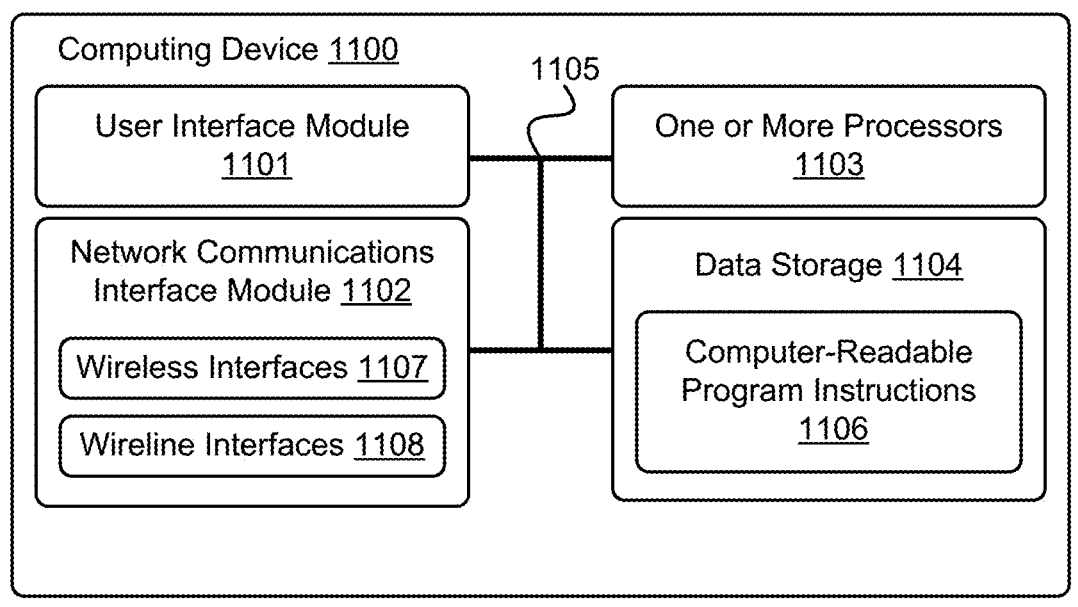
FIG. 11 is a block diagram of a computing device, in accordance with an example embodiment.

FIG. 11 is a block diagram of a computing device (e.g., system) in accordance with an example embodiment. In particular, computing device 1100 shown in FIG. 11 can be configured to perform part or all of methods 100 and 200 and/or some or all of the herein-described functionality of EHR systems 310, 320, 400, 452, computing devices 402, 450, network 444, database server 460, 462, 464, radiological EHR system 800, and/or a patient discharge EHR system 900.

Computing device 1100 may include a user interface module 1101, a network-communication interface module 1102, one or more processors 1103, and data storage 1104, all of which may be linked together via a system bus, network, or other connection mechanism 1105.

User interface module 1101 can be configured to send and/or receive data from external user input and/or user output devices. For example, user interface module 1101 can be configured to send and/or receive data to and/or from user input devices such as a keyboard, a keypad, a touch screen, a computer mouse, a track ball, a joystick, a camera, a voice recognition module, and/or other similar devices. User interface module 1101 can also be configured to provide output to user display devices, such as one or more cathode ray tubes (CRT), liquid crystal displays (LCDs), light emitting diodes (LEDs), displays using digital light processing (DLP) technology, printers, light bulbs, and/or other similar devices, either now known or later developed. User interface module 1101 can also be configured to generate audible output(s), such as a speaker, speaker jack, audio output port, audio output device, earphones, and/or other similar devices.

Network-communications interface module 1102 can include one or more wireless interfaces 1108 and/or one or more wireline interfaces 1108 configured to communicate via a network; e.g., network 1006 of FIG. 10. Wireless interfaces 1108 can include one or more wireless transmitters, receivers, and/or transceivers, such as a Bluetooth transceiver, a Zigbee transceiver, a Wi-Fi transceiver, a WiMAX transceiver, a wireless WAN transceiver (e.g., a transceiver for one or more LTE, GSM, CDMA, and/or TDMA networks) and/or other similar type of wireless transceiver configurable to communicate via a wireless network. Wireline interfaces 1108 can include one or more wireline transmitters, receivers, and/or transceivers, such as an Ethernet transceiver, a Universal Serial Bus (USB) transceiver, or similar transceiver configurable to communicate via a twisted pair wire, a coaxial cable, a fiber-optic link, or a similar physical connection to a wireline network.

In some embodiments, network communications interface module 1102 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and DSA. Other cryptographic protocols and/or algorithms can be used as well or in addition to those listed herein to secure (and then decrypt/decode) communications.

Processors 1103 can include one or more general purpose processors and/or one or more special purpose processors (e.g., digital signal processors, application specific integrated circuits, etc.). Processors 1103 can be configured to execute computer-readable program instructions 1106 that are contained in the data storage 1104 and/or other instructions as described herein.

Data storage 1104 can include one or more computer-readable storage media that can be read and/or accessed by at least one of processors 1103. For example, data storage 1104 can provide memory for the herein-described application spaces and non-application spaces; i.e., part or all of data storage 1104 can be divided into application space(s) and non-application space(s). The one or more computer-readable storage media can include volatile and/or non-volatile storage components, such as optical, magnetic, organic or other memory or disc storage, which can be integrated in whole or in part with at least one of processors 1103. In some embodiments, data storage 1104 can be implemented using a single physical device (e.g., one optical, magnetic, organic or other memory or disc storage unit), while in other embodiments, data storage 1104 can be implemented using two or more physical devices.

Data storage 1104 can include computer-readable program instructions 1106. In some embodiments, data storage 1104 can additionally include storage required to perform at least part of the herein-described methods and techniques and/or at least part of the functionality of the herein-described devices and networks.

Example methods and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

It should be understood that other embodiments can include more or less of each element shown in a given figure. Further, some of the illustrated elements can be combined or omitted. Yet further, an example embodiment can include elements that are not illustrated in the figures.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

Moreover, a block that represents one or more information transmissions may correspond to information transmissions between software and/or hardware modules in the same physical device. However, other information transmissions may be between software modules and/or hardware modules in different physical devices.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, and/or a tangible storage device.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A method, comprising:

receiving, from a user at a first electronic health records (EHR) system resident on a first computing device, a request to report information about a patient to a second EHR system resident on the first computing device or a second computing device, wherein the first and second EHR systems have previously established one or more matching pseudonyms, wherein the one or more matching pseudonyms are different from a first user name used by the user to login to the first EHR system, wherein the one or more matching pseudonyms are associated with a previously established context for the user and the patient;

responsive to the request, generating an EHR report using the first EHR system, wherein the EHR report comprises at least the one or more previously established matching pseudonyms; and sending the EHR report from the first EHR system to the second EHR system, wherein the EHR report is sent via memory transfer if the second EHR system is resident on the first computing device or via a network if the second EHR system is resident on the second computing device, wherein the EHR report automatically authenticates the user to access patient information of the patient at the second EHR system based on the previously established context for the user and the patient using the one or more previously established matching pseudonyms without requiring user intervention by the user to login to the second EHR system.

2. The method of claim 1, wherein the one or more matching pseudonyms comprise at least a matching user pseudonym.

3. The method of claim 1, wherein the one or more matching pseudonyms comprise at least a matching patient pseudonym.

4. The method of claim 1, wherein the one or more matching pseudonyms comprise at least a matching patient visit pseudonym identifying a medical session with the patient.

5. The method of claim 1, wherein the EHR report comprises a single line that consists of the one or more matching pseudonyms, a timestamp, and a hash value for the pseudonyms and the timestamp.

6. The method of claim 1, wherein the one or more matching pseudonyms correspond to one or more of an EHR-user identifier, an EHR-patient identifier, or a behavior identifier.

7. The method of claim 1, wherein the one or more matching pseudonyms comprise one or more context-related pseudonyms for specialized functions of the second EHR system.

8. The method of claim 1, wherein the one or more matching pseudonyms correspond to a behavior identifier, and wherein the second EHR system provides an output based on the behavior identifier.

9. The method of claim 1, wherein the patient is a new patient of the second EHR system, and wherein the EHR report authorizes the user to add the new patient to the second EHR system and access patient information of the new patient using the one or more matching pseudonyms without requiring user intervention by the user to login to the second EHR system.

10. The method of claim 1, wherein the second EHR system comprises a patient discharge EHR system, and wherein the second EHR system generates one or more discharge instructions for the patient.

11. The method of claim 1, wherein the second EHR system comprises a radiological EHR system, and wherein the second EHR system displays radiological information for the patient.

12. The method of claim 1, wherein the first EHR system is configured to authenticate users before using the first EHR system, and wherein the second EHR system is configured to authenticate users before using the second EHR system.

13. The method of claim 1, wherein the EHR report comprises a hash value, and wherein the second EHR system authenticates the user based on the hash value in the EHR report.

14. The method of claim 13, wherein the EHR report comprises a timestamp, and wherein the second EHR system authenticates the user based on the hash value in the EHR report only within a predetermined amount of time of the timestamp.

15. The method of claim 13, wherein the EHR report comprises a timestamp, and wherein the second EHR system calculates the hash value using a hash function operating on hashing data, wherein the hashing data includes the one or more matching pseudonyms and the timestamp.

16. The method of claim 1, wherein the EHR report comprises a computing-device identifier identifying a computing device, and wherein the second EHR system authenticates the user based on the one or more matching pseudonyms only when the EHR report is sent from the computing device identified by the computing-device identifier.

17. The method of claim 1, wherein the one or more matching pseudonyms correspond to a behavior identifier indicating to update a patient record for the patient at the second EHR system.

18. The method of claim 1, wherein the one or more matching pseudonyms correspond to a behavior identifier indicating to delete a patient record for the patient at the second EHR system.

19. A first computing device, comprising:

one or more processors; and non-transient computer readable memory, configured to store executable instructions that, upon execution by the one or more processors, cause the first computing device to perform functions comprising:

receiving, from a user at first electronic health records (EHR) system resident on the first computing device, a request to report information about a patient to a second EHR system resident on the first computing device or a second computing device, wherein the first and second EHR systems have previously established one or more matching pseudonyms, wherein the one or more matching pseudonyms are different from a first user name used by the user to login to the first EHR system, wherein the one or more matching pseudonyms are associated with a previously established context for the user and the patient;

responsive to the request, generating an EHR report using the first EHR system, wherein the EHR report comprises at least the one or more previously established matching pseudonyms; and sending the EHR report from the first EHR system to the second EHR system, wherein the EHR report is sent via memory transfer if the second EHR system is resident on the first computing device or via a network if the second EHR system is resident on the second computing device, wherein the EHR report automatically authenticates the user to access patient information of the patient at the second EHR system based on the previously established context for the user and the patient using the one or more previously established matching pseudonyms without requiring user intervention by the user to login to the second EHR system.

20. A non-transient computer readable memory of a first first computing device, the memory configured to store executable instructions that, upon execution by one or more processors of the first computing device, cause the first computing device to perform functions comprising:

receiving, from a user at a first EHR system resident on the first computing device, a request to report information about a patient to a second EHR system resident on the first computing device or a second computing device, wherein the first and second EHR systems have previously established one or more matching pseudonyms, wherein the one or more matching pseudonyms are different from a first user name used by the user to login to the first EHR system, wherein the one or more matching pseudonyms are associated with a previously established context for the user and the patient;

responsive to the request, generating an EHR report using the first EHR system, wherein the EHR report comprises at least the one or more previously established matching pseudonyms; and sending the EHR report from the first EHR system to the second EHR system, wherein the EHR report is sent via memory transfer if the second EHR system is resident on the first computing device or via a network if the second EHR system is resident on the second computing device, wherein the EHR report automatically authenticates the user to access patient information of the patient at the second EHR system based on the previously established context for the user and the patient using the one or more previously established matching pseudonyms without requiring user intervention by the user to login to the second EHR system.

* * * * *